United States Patent
Samain et al.

(10) Patent No.: US 6,749,837 B1
(45) Date of Patent: *Jun. 15, 2004

(54) COSMETIC COMPOSITION COMPRISING AT LEAST A FILM-FORMING POLYMER AND AT LEAST A REGULATING AGENT

(75) Inventors: Henri Samain, Bièvres (FR); Christine Dupuis, Paris (FR)

(73) Assignee: L'Oreal S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,505

(22) PCT Filed: Nov. 10, 2000

(86) PCT No.: PCT/FR00/03148

§ 371 (c)(1), (2), (4) Date: Oct. 12, 2001

(87) PCT Pub. No.: WO01/35911

PCT Pub. Date: May 25, 2001

(30) Foreign Application Priority Data

Nov. 19, 1999 (FR) .............................. 99 14596

(51) Int. Cl.$^7$ ............................ A61K 7/00; A61K 7/42; A61K 7/04; A61K 7/06; A61K 31/74

(52) U.S. Cl. .............................. 424/47; 424/59; 424/61; 424/70.1; 424/70.9; 424/70.11; 424/70.12; 424/70.14; 424/70.21; 424/70.22; 424/70.27; 424/70.31; 424/78.03; 424/400; 424/401; 424/DIG. 1; 424/DIG. 2; 514/945

(58) Field of Search .............................. 424/400, 401, 424/59, 61, 47, 70.1, 70.9, 70.11, 70.12, 70.14, 70.21, 70.22, 70.27, 70.31, 78.03, DIG. 1, DIG. 2; 514/945

(56) References Cited

U.S. PATENT DOCUMENTS

5,965,111 A * 10/1999 Ellingson et al. .............. 424/61
6,391,292 B1 * 5/2002 Samain et al. .......... 424/70.11

FOREIGN PATENT DOCUMENTS

| DE | 198 38 851 | 3/2000 |
| EP | 0 960 893 | 12/1999 |
| WO | WO 98/03148 | 1/1998 |
| WO | WO 99/55290 | 11/1999 |
| WO | WO 99/56710 | 11/1999 |

OTHER PUBLICATIONS

"Avalure$^{TM}$ Film Forming Polymers for Personal Care Applications", Noveon, TDS–248, Jun. 19, 2001, pp. 1–4.

English language Derwent Abstract of DE 198 38 851, Mar. 2, 2000.

* cited by examiner

Primary Examiner—Thurman K. Page
Assistant Examiner—Marina Lamm
(74) Attorney, Agent, or Firm—Finnegan, Henderson, Farabow, Garrett & Dunner, L.L.P.

(57) ABSTRACT

The invention concerns a cosmetic composition comprising, in a cosmetically acceptable medium, at least a film-forming polymer (A) with particular characteristics and at least an additive (B), the latter being selected such that the film formed on the hair after the cosmetic composition has been applied retains its mechanical properties whatever the hygrometric condition. The invention also concerns a hair care or hair styling method using said composition and its use for the formulation of cosmetic products such as lacquers, sprays or foams, for hair care or hair styling.

53 Claims, No Drawings

COSMETIC COMPOSITION COMPRISING AT LEAST A FILM-FORMING POLYMER AND AT LEAST A REGULATING AGENT

The invention relates to a cosmetic composition comprising, in a cosmetically acceptable medium, at least one film-forming polymer (A) with specific characteristics and at least one additive (B), the latter being chosen such that the film formed on the hair after applying the cosmetic composition keeps its mechanical properties irrespective of the hygrometric conditions. The invention is also directed towards a process for shaping or holding the hair using this composition, as well as to its use for formulating cosmetic products such as lacquers, sprays or mousses, in order to hold or shape the hair style.

The compositions in accordance with the invention can be applied to the skin, the nails, the lips, the hair, the eyebrows or the eyelashes.

For the purposes of the present invention, the expression "styling composition" means compositions for holding and/or fixing the hair.

Among the haircare products for fixing the hair that are most widely available on the cosmetics market, mention may be made of compositions for spraying as an aerosol or in a pump-dispenser bottle such as lacquers, sprays or mousses, consisting essentially of a solution, usually an alcoholic or aqueous-alcoholic solution, and of a film-forming polymer which is soluble in water or in alcohol, mixed with various cosmetic adjuvants.

After application to the hair, these haircare products generally form a film which holds the hair style in the shape desired by the user. By appropriately selecting the polymers present in the composition, it is already possible to modify the mechanical properties of this film, such as the hardness, the elasticity or the elongation at break, and to do so under given humidity and temperature conditions.

However, these mechanical properties are generally dependent on the external conditions, such as the hygrometric conditions. Thus, a haircare composition which gives a film with satisfactory properties under certain humidity conditions can give poorer results under other humidity conditions, for example a soft film which does not hold the hair style.

There is thus a need to find formulations for holding and/or fixing the hair style whose mechanical performance qualities, in particular the elasticity and flexibility, are maintained irrespective of the hygrometric conditions, and in particular in passing from a humid atmosphere to a dry atmosphere.

The Applicant has discovered, surprisingly and unexpectedly, that it is possible to overcome the technical problem mentioned above by using certain specific combinations of film-forming polymer(s) and additive(s)

A subject of the invention is a cosmetic composition comprising, in a cosmetically acceptable medium:
(1) at least one film-forming polymer (A) chosen such that a film obtained by drying a mixture of this polymer (A) with ethanol or water, under a humid atmosphere, has a mechanical profile defined by at least:
  (i) an elongation at break ($\epsilon_r$) of greater than or equal to 160%;
  (ii) a recovery at 300 seconds ($R_{300}$) of greater than or equal to 45%; and
(2) at least one additive (B) chosen from linear, non-oxyalkylenated, functionalized or unfunctionalized silicones, oxyalkylenated silicones, alkyl ethers of alkylene glycols or of polyalkylene glycols comprising $C_1$ to $C_{15}$ alkyl groups and polyurethanes comprising polyether and/or polycarbonate units.

Another subject of the present invention relates to a process for shaping or holding the hair style, comprising the use of this composition.

Yet another subject of the present invention relates to the use of at least one additive (B) chosen from linear, non-oxyalkylenated, functionalized or unfunctionalized silicones, oxyalkylenated silicones, alkyl ethers of alkylene glycols or of polyalkylene glycols comprising $C_1$ to $C_{15}$ alkyl groups, and polyurethanes comprising polyether and/or polycarbonate units, in cosmetic compositions, in order to maintain the mechanical profile of the film obtained by drying the said cosmetic composition, in passing from a humid atmosphere to a dry atmosphere.

One most particular subject of the invention relates to the use of at least one such additive (B) in a cosmetic composition comprising at least one film-forming polymer (A) chosen such that a film obtained by drying a mixture of the said composition, under humid or dry atmosphere, has a mechanical profile defined by at least:
  (i) an elongation at break ($\epsilon_r$) of greater than or equal to 160%;
  (ii) a recovery at 300 seconds ($R_{300}$) of greater than or equal to 45%.

These characteristics are reflected by a maintenance of the flexibility and elasticity qualities of the films irrespective of the level of humidity. This explains the constancy of the results of holding on hair, independently of the level of humidity.

The polymers (A) that are particularly targeted by the present invention are those distributed by Goodrich under the name Avalure AC 315® and V29®.

For the purposes of the present invention, the expression "humid atmosphere" means, for example, the environment obtained by an atmosphere of air with a water vapour content of about 12 grams to 13 grams per kilogram of dry air, and the expression "dry atmosphere" means, for example, the environment obtained by an air atmosphere with a water vapour content of about 7 grams per kilogram of dry air.

For the purposes of the present invention, the expression "film obtained by drying under a humid or dry atmosphere" means the film obtained under these conditions starting with a mixture containing 6% active material (a.m.) of polymer A, alone or in the presence of the additive B, with ethanol or water, the amount of mixture being adapted to obtain in a Teflon matrix a film 500±50 µm thick. The drying is continued until the weight of the film no longer changes, which represents about 12 days. The polymers A that are soluble or partially soluble in ethanol are tested in ethanol. The other polymers are tested in water in soluble or dispersed form.

For the purposes of the present invention, the elongation at break and the degree of recovery are evaluated by means of the tests described below.

To carry out the tensile tests, the film is cut into rectangular samples 80 mm long and 15 mm wide.

The tests are carried out on a machine sold under the name Lloyd or sold under the name Zwick under the same conditions as for the drying, i.e. a water vapour content in the atmosphere of 13 grams per kilogram of dry air.

The samples are drawn at a speed of 20 mm/min and the distance between the jaws is 50±1 mm.

To determine the instantaneous recovery ($R_i$), the following is performed:
  the sample is drawn to 150% ($\epsilon_{max}$), i.e. to 1.5 times its initial length ($l_0$)

the stress is removed by imposing a return speed equal to the tensile speed, i.e. 20 mm/min, and the elongation of the sample is measured as a percentage, after return at zero load ($\epsilon_i$).

The percentage instantaneous recovery ($R_i$) is given by the formula below:

$$R_i = ((\epsilon_{max} - \epsilon_i)/\epsilon_{max}) \times 100$$

In order to determine the recovery at 300 seconds, the sample which has undergone the above operations is maintained at zero stress for a further 300 seconds and the percentage elongation ($R_{300}$) is measured.

The percentage recovery at 300 seconds ($R_{300}$) is given by the formula below:

$$R_{300} = ((\epsilon_{max} - \epsilon_{300})/\epsilon_{max}) \times 100$$

For the purposes of the present invention, the expression "non-oxyalkylenated silicone" means any organosilicon polymer or oligomer of linear, branched or crosslinked structure and of variable molecular weight, which is volatile or non-volatile, obtained by polymerization and/or polycondensation of suitably functionalized silanes, and consisting essentially of a repetition of main units in which the silicon atoms are linked together via oxygen atoms, forming a siloxane bond ≡Si—O—Si≡, optionally substituted hydrocarbon-based radicals being linked directly via a carbon atom to the said silicon atoms. The hydrocarbon-based radicals that are most common are alkyl radicals, especially $C_1$–$C_{10}$ alkyl radicals and in particular methyl, as well as fluoroalkyl radicals.

The non-oxyalkylenated silicones can be polydialkylsiloxanes, in particular polydimethyl-siloxanes, or polyarylsiloxanes such as polyphenyl-siloxanes, or polyalkylarylsiloxanes, such as polymethylphenylsiloxanes.

The non-oxyalkylenated silicones can also be modified, for example with carboxylic groups.

The products sold under the brand name Oil M 642, SLM 23 000/1 or SLM 23 000/2 by the company Wacker, or alternatively under the brand name 176-12057 by the company General Electric, or alternatively under the brand name FZ 3703 by the company OSI, or alternatively under the brand name BY 16 880 by the company Toray Silicone are advantageously used.

The number-average molecular mass of the silicone polymer is preferably between 10,000 and 1,000,000 approximately, and even more preferably between 10,000 and 100,000 approximately.

Other non-oxyalkylenated silicones that are particularly suitable for carrying out the present invention are silicones comprising at least one substituent containing at least two identical or different groups chosen from carboxylic acids or salts thereof, amides and esters, at least one of these groups being a carboxylic acid or salts thereof.

Such silicones are sold, for example, under the brand name SLM 23 105 by the company Wacker and under the brand name Densodrin OF by the company BASF.

Volatile silicones can also be used.

Other types of non-oxyalkylenated silicones which may be mentioned are those modified with alkoxy, sulphonate, thiol, hydroxyl, amino or hydroxyacylamino groups.

In accordance with the invention, the oxyalkylenated silicones are preferably chosen from the compounds of general formula (I):

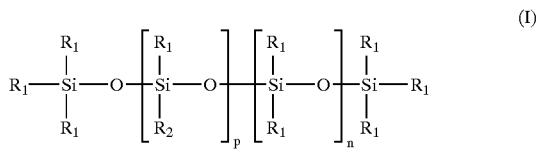

(I)

in which formula:
$R_1$, which may be identical or different, represents a hydrogen atom or a $C_1$–$C_{30}$ linear or branched alkyl radical,
$R_2$, which may be identical or different, represents $(C_xH_{2x})$—$(OC_2H_4)_a$—$(OC_3H_6)_b$—$OR_3$,
$R_3$, which may be identical or different, is chosen from a hydrogen atom, a linear or branched alkyl radical containing from 1 to 12 carbon atoms, and a linear or branched acyl radical containing from 2 to 12 carbon atoms,
n ranges from 0 to 1000,
p ranges from 1 to 8,
a ranges from 0 to 50,
b ranges from 0 to 50,
a+b is greater than or equal to 1,
x ranges from 1 to 5,
the number-average molecular weight being greater than or equal to 15,000 and preferably between 25,000 and 75,000.

The oxyalkylenated silicones that are preferably used are those of general formula (I) which satisfy at least one and preferably all of the following conditions:
$R_1$ denotes a methyl radical,
$R_3$ represents a hydrogen atom, a methyl radical or an acetyl radical and preferably hydrogen,
p ranges from 2 to 6,
a is between 5 and 40 and preferably between 15 and 30,
b is between 5 and 40 and preferably between 15 and 30,
x is equal to 2 or 3,
n ranges from 20 to 600, preferably from 50 to 500 and even more particularly from 200 to 500.

Such silicones are disclosed, for example, in U.S. Pat. No. 4,311,695 which is included by way of reference.

The silicones that are most particularly preferred are, for example, those sold as a 10% by weight solution in a cyclomethicone (Dow Corning 344) under the trade name Fluid DC 3225 C by the company Dow Corning or the product sold under the name Silwet L 7001 by the company Union Carbide, as well as the product sold by Dow Corning under the name DC 190.

Among the polyurethanes which may be used as additive (s) (B) in the context of the present invention, mention may be made in particular of anionic, cationic, nonionic or amphoteric polyurethanes, such as polyurethane-acrylics, polyurethane-polyvinylpyrrolidones, polyester-polyurethanes, polyether-polyurethanes, polyureas and polyurea/polyurethanes, and mixtures thereof.

The polyurethane can be, for example, an aliphatic, cycloaliphatic or aromatic polyurethane, polyurea/urethane or polyurea copolymer comprising, alone or as a mixture,
at least one block of linear or branched aliphatic and/or cycloaliphatic and/or aromatic polyester origin, and/or
at least one block of aliphatic and/or cycloaliphatic and/or aromatic polyether origin, and/or
at least one substituted or unsubstituted, branched or unbranched silicone block, for example polydimethylsiloxane or polymethylphenylsiloxane, and/or
at least one block comprising fluoro groups.

The polyurethanes as defined in the invention can also be obtained from branched or unbranched polyesters, or from alkyds comprising labile hydrogens which are modified by reaction with a diisocyanate and a difunctional organic compound (for example dihydro, diamino or hydroxyamino), also comprising either a carboxylic acid or carboxylate group, or a sulphonic acid or sulphonate group, or alternatively a neutralizable tertiary amine group or a quaternary ammonium group.

The polyurethanes that are particularly targeted by the present invention are the polyurethanes PA Marin UA200® and PA Marin UA310® sold by Sanyo, and Polyderm R sold by Alzo.

Among the alkyl ethers of alkylene glycols and of polyalkylene glycols which can be used as additive(s) (B) in the compositions according to the invention, mention may be made in particular of diethylene glycol ethyl ether, diethylene glycol methyl ether, diethylene glycol butyl ether or diethylene glycol hexyl ether, dipropylene glycol butyl ether, tripropylene glycol butyl ether, dipropylene glycol ethyl ether, tripropylene glycol methyl ether and diethylene glycol methyl ether, and mixtures thereof.

Additives (B) that are preferably used are oxyalkylenated silicones and polyurethanes, and among these additives, polyurethane-polyethers are preferred.

In the compositions in accordance with the invention, the film-forming polymer(s) (A) is (are) preferably present at concentrations of between 0.05% and 20% by weight, more preferably between 0.1% and 15% by weight, and more preferably between 0.25% and 10% by weight relative to the total weight of the composition.

The additive (B) is preferably a non-oxyalkylenated silicone modified with one or more carboxylic, alkoxy, sulphonate, thiol, hydroxyl, amino or hydroxyacylamino groups, or unmodified such as polydialkylsiloxane, polyarylsiloxane or polyalkyl-arylsiloxane.

In the compositions in accordance with the invention, the additive(s) (B) is (are) preferably present at concentrations of between 0.05% and 20% by weight, more preferably between 0.1% and 15% by weight and more preferably between 0.25% and 10% by weight, relative to the total weight of the composition.

The concentrations of polymer(s) (A) and of additives (B) are advantageously chosen such that the ratio of the concentration of polymer (A) to the concentration of polymer (B) is between 4000 and 0.002.

The cosmetically acceptable medium preferably consists of water or one or more cosmetically acceptable solvents such as alcohols or water-solvent(s) mixtures, these solvents preferably being $C_1$–$C_4$ alcohols.

Among these alcohols which may be mentioned are ethanol and isopropanol. Ethanol is particularly preferred.

The composition of the invention can also contain at least one conventional cosmetic additive chosen from thickeners, anionic, nonionic, cationic or amphoteric surfactants, fragrances, preserving agents, sunscreens, proteins, vitamins, provitamins, fixing or non-fixing, anionic, nonionic, cationic or amphoteric polymers other than those of the invention, mineral, plant or synthetic oils, ceramides, pseudoceramides and any other additive conventionally used in cosmetic compositions intended to be applied to the hair.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

These compositions can be packaged in various forms, in particular in pump-dispenser bottles or in aerosol containers, in order to apply the composition in vaporized form or in the form of a mousse. Such packaging forms are indicated, for example, when it is desired to obtain a spray, a lacquer or a mousse for fixing or treating the hair. The compositions in accordance with the invention can also be in the form of creams, gels, emulsions, lotions or waxes.

When the composition according to the invention is packaged in aerosol form in order to obtain a lacquer or a mousse, it comprises at least one propellant which can be chosen from volatile hydrocarbons such as n-butane, propane, isobutane and pentane, a halohydrocarbon and mixtures thereof. Carbon dioxide, nitrous oxide, dimethyl ether (DME), nitrogen or compressed air can also be used as propellant. Mixtures of propellants can also be used. Dimethyl ether is preferably used.

The propellant is advantageously present at a concentration of between 5% and 90% by weight relative to the total weight of the composition in the aerosol device, and more particularly at a concentration of between 10% and 60%.

The compositions in accordance with the invention can be applied to wet or dry hair.

The invention will be illustrated more fully with the aid of the non-limiting example which follows.

All the percentages are relative percentages by weight relative to the total weight of the composition, and a.m. means active material.

EXAMPLE

Two compositions for holding and/or fixing the hair style in accordance with the present invention are prepared comprising, as polymer (A), Avalure AC315, and as additive (B), either the polyurethane PA Marin UA 200® sold by Sanyo, or the silicone DC 190 sold by Dow Corning. A composition in accordance with the prior art comprising only Avalure AC315 is also prepared. Table 1 below summarizes the formulations prepared.

TABLE 1

|  | Composition 1 (prior art) | Composition 2 (invention) | Composition 3 (invention) |
| --- | --- | --- | --- |
| Avalure AC315 | 6% | 5% | 5% |
| PA Marin UA200 | — | 1% | — |
| Silicone DC190 | — | — | 1% |
| Ethanol | q.s. 100 | q.s. 100 | q.s. 100 |

The flexibility and elasticity of the film formed using compositions 1 to 3 are evaluated in humid and dry atmosphere. A sensory test is used for this. The grades range from 0 (poor performance) to 5 (excellent performance). The results obtained are summarized in Table 2 below.

TABLE 2

|  | Appearance of the films | |
| --- | --- | --- |
| Composition | Humid atmosphere | Dry atmosphere |
| 1 (prior art) | Flexibility 4 elasticity 3 | Flexibility 2 elasticity 1 |
| 2 (invention) | Flexibility 4 elasticity 2 | Flexibility 4 elasticity 2.5 |
| 3 (invention) | Flexibility 4 elasticity 3 | Flexibility 4 elasticity 3 |

It results therefrom that the flexibility and elasticity of the films obtained on the hair by drying the compositions in accordance with the invention comprising a polymer (A) and an additive (B) are virtually constant, in passing from a dry atmosphere to a humid atmosphere. Conversely, the variation of these properties is marked for the composition in accordance with the prior art comprising Avalure AC315 alone, both as regards the flexibility and the elasticity.

Compositions 1 to 3 packaged in aerosol form (65% fluid, 35% DME) are applied to wigs made of European chestnut-brown hair. After conditioning these wigs for 2 hours in a humid or dry atmosphere, a panel of experts grades the hold of the hair style. The following results collated in Table 3 below are obtained.

TABLE 3

| Composition | Humid atmosphere | Dry atmosphere |
| --- | --- | --- |
| 1 (prior art) | Good hold | Poor hold |
| 2 (invention) | Good hold | Good hold |
| 3 (invention) | Good hold | Good hold |

It results therefrom that only Compositions 2 and 3 according to the invention provide hold independently of the degree of humidity.

What is claimed is:

1. A cosmetic composition comprising:
   (1) at least one film-forming polymer (A), wherein a film obtained by drying a mixture of said at least one film-forming polymer (A) with ethanol or water, under a humid atmosphere, has a mechanical profile defined by at least:
      (i) an elongation at break ($\epsilon_r$) of greater than or equal to 160%; and
      (ii) a recovery at 300 seconds ($R_{300}$) of greater than or equal to 45%; and
   (2) at least one additive (B) chosen from oxyalkylenated silicones chosen from compounds of formula (I):

$$R_1-\underset{\underset{R_1}{|}}{\overset{\overset{R_1}{|}}{Si}}-O-\left[\underset{\underset{R_2}{|}}{\overset{\overset{R_1}{|}}{Si}}-O\right]_p\left[\underset{\underset{R_1}{|}}{\overset{\overset{R_1}{|}}{Si}}-O\right]_n\underset{\underset{R_1}{|}}{\overset{\overset{R_1}{|}}{Si}}-R_1 \quad (I)$$

wherein:
   $R_1$, which may be identical or different, is chosen from hydrogen and $C_1$–$C_{30}$ linear and branched alkyl radicals,
   $R_2$, which may be identical or different, is chosen from —$(C_xH_{2x})$—$(OC_2H_4)_a$—$(OC_3H_6)_b$—$OR_3$,
   $R_3$, which may be identical or different, is chosen from hydrogen, linear and branched alkyl radicals containing from 1 to 12 carbon atoms, and linear and branched acyl radicals containing from 2 to 12 carbon atoms,
   n ranges from 0 to 1000,
   p ranges from 1 to 8,
   a ranges from 0 to 50,
   b ranges from 0 to 50,
   a+b is greater than or equal to 1,
   x ranges from 1 to 5, and
   the number-average molecular weight is greater than or equal to 15,000.

2. The composition according to claim 1, further comprising a cosmetically acceptable medium.

3. The composition according to claim 1, wherein the number-average molecular weight ranges from about 25,000 to about 75,000.

4. The composition according to claim 1, wherein said at least one film-forming polymer (A) is present at a concentration ranging from about 0.05% to about 20% by weight, relative to the total weight of the composition.

5. The composition according to claim 4, wherein said at least one film-forming polymer (A) is present at a concentration ranging from about 0.1% to about 15% by weight, relative to the total weight of the composition.

6. The composition according to claim 5, wherein said at least one film-forming polymer (A) is present at a concentration ranging from about 0.25% to about 10% by weight, relative to the total weight of the composition.

7. The composition according to claim 1, wherein said at least one additive (B) is present at a concentration ranging from about 0.05% to about 20% by weight, relative to the total weight of the composition.

8. The composition according to claim 7, wherein said at least one additive (B) is present at a concentration ranging from about 0.1% to about 15% by weight, relative to the total weight of the composition.

9. The composition according to claim 8, wherein said at least one additive (B) is present at a concentration ranging from about 0.25% to about 10% by weight, relative to the total weight of the composition.

10. The composition according to claim 1, wherein the ratio of the concentration of said at least one film-forming polymer (A) to the concentration of said at least one additive (B) ranges from about 4000:1 to about 0.002:1.

11. The composition according to claim 1, further comprising at least one cosmetic additive chosen from thickeners; anionic, nonionic, cationic and amphoteric surfactants; fragrances; preserving agents; sunscreens; proteins; vitamins; provitamins; fixing and non-fixing, anionic, nonionic, cationic and amphoteric polymers other than those defined in claim 1; mineral, plant and synthetic oils; ceramides; pseudoceramides; and any other suitable additive used in cosmetic compositions.

12. An aerosol device containing a cosmetic composition comprising:
   (1) at least one film-forming polymer (A) in said aerosol device, wherein a film obtained by drying a mixture of said at least one film-forming polymer (A) with ethanol or water, under a humid atmosphere, has a mechanical profile defined by at least:
      (i) an elongation at break ($\epsilon_r$) of greater than or equal to 160%; and
      (ii) a recovery at 300 seconds ($R_{300}$) of greater than or equal to 45%; and
   (2) in said aerosol device at least one additive (B) chosen from: linear, non-oxyalkylenated, functionalized and unfunctionalized silicones, oxyalkylenated silicones, alkyl ethers of alkylene glycols and of polyalkylene glycols comprising $C_1$ to $C_{15}$ aldyl groups, and polyuethanes comprising at least one unit chosen from polyether and polycarbonate units, said ingredients (1) and (2) being present in said aerosol device.

13. The aerosol device according to claim 12, further comprising a cosmetically acceptable medium.

14. The aerosol device according to claim 12, wherein said at least one additive (B) is chosen from non-oxyalkylenated silicones modified with at least one group chosen from: carboxylic, alkoxy, sulphonate, thiol, hydroxyl, amino, and hydroxyacylamino groups.

15. The aerosol device according to claim 12, wherein said at least one additive (B) is chosen from unmodified non-oxyalkylenated silicones.

16. The aerosol device according to claim 15, wherein said unmodified non-oxyalkylenated silicones are chosen from polydialkylsiloxane, polyarylsiloxane, and polyalkylarylsiloxane.

17. The aerosol device according to claim 12, wherein said at least one additive (B) is chosen from oxyalkylenated silicones chosen from compounds of formula (I):

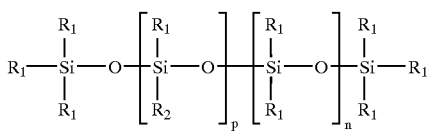

wherein:
R$_1$, which may be identical or different, is chosen from hydrogen and C$_1$–C$_{30}$ linear and branched alkyl radicals,
R$_2$, which may be identical or different, is chosen from —(C$_x$H$_{2x}$)—(OC$_2$H$_4$)$_a$—(OC$_3$H$_6$)$_b$—OR$_3$,
R$_3$, which may be identical or different, is chosen from hydrogen, linear and branched alkyl radicals containing from 1 to 12 carbon atoms, and linear and branched acyl radicals containing from 2 to 12 carbon atoms,
n ranges from 0 to 1000,
p ranges from 1 to 8,
a ranges from 0 to 50,
b ranges from 0 to 50,
a+b is greater than or equal to 1,
x ranges from 1 to 5, and
the number-average molecular weight is greater than or equal to 15,000.

18. The aerosol device according to claim 17, wherein the number-average molecular weight ranges from about 25,000 to about 75,000.

19. The aerosol device according to claim 12, wherein said at least one additive (B) is chosen from polyurethanes chosen from: anionic, cationic, nonionic, and amphoteric polyurethanes.

20. The aerosol device according to claim 12, wherein said at least one additive (B) is chosen from polyurethane-polyethers.

21. The aerosol device according to claim 12, wherein said at least one additive (B) is chosen from: alkyl ethers of an alkylene glycol and of a polyalkylene glycol chosen from diethylene glycol ethyl ether, diethylene glycol methyl ether, diethylene glycol butyl ether, diethylene glycol hexyl ether, dipropylene glycol butyl ether, tripropylene glycol butyl ether, dipropylene glycol ethyl ether, tripropylene glycol methyl ether and diethylene glycol methyl ether.

22. The aerosol device according to claim 12, wherein said at least one film-forming polymer (A) is present at a concentration ranging from about 0.05 to about 20% by weight, relative to the total weight of the composition.

23. The aerosol device according to claim 22, wherein said at least one film-forming polymer (A) is present at a concentration ranging from about 0.1% to about 15% by weight, relative to the total weight of the composition.

24. The aerosol device according to claim 23, wherein said at least one film-forming polymer (A) is present at a concentration ranging from about 0.25% to about 10% by weight, relative to the total weight of the composition.

25. The aerosol device according to claim 12, wherein said at least one additive (B) is present at a concentration ranging from about 0.05% to about 20% by weight, relative to the total weight of the composition.

26. The aerosol device according to claim 25, wherein said at least one additive (B) is present at a concentration ranging from about 0.1% to about 15% by weight, relative to the total weight of the composition.

27. The aerosol device according to claim 26, wherein said at least one additive (B) is present at a concentration ranging from about 0.25% to about 10% by weight, relative to the total weight of the composition.

28. The aerosol device according to claim 12, wherein the ratio of the concentration of said at least one film-forming polymer (A) to the concentration of said at least one additive (B) ranges from about 4000:1 to about 0.002:1.

29. The aerosol device according to claim 12, further comprising at least one cosmetic additive chosen from thickeners; anionic, nonionic, cationic and amphoteric surfactants; fragrances; preserving agents; sunscreens; proteins; vitamins; provitamins; fixing and non-fixing, anionic, nonionic, cationic and amphoteric polymers other than those defined in claim 12; mineral, plant and synthetic oils; ceramides; pseudoceramides; and any other suitable additive used in cosmetic compositions.

30. A hair styling product comprising a composition comprising:
  (1) at least one film-forming polymer (A) in said hair styling product, wherein a film obtained by drying a mixture of said at least one film-forming polymer (A) with ethanol or water, under a humid atmosphere, has a mechanical profile defined by at least:
    (i) an elongation at break ($\epsilon_r$) of greater than or equal to 160%; and
    (ii) a recovery at 300 seconds (R$_{300}$) of greater than or equal to 45%; and
  (2) in said hair styling product at least one additive (B) chosen from: linear, non-oxyalkylenated, functionalized and unfunctionalized silicones, oxyalkylenated silicones, alkyl ethers of alkylene glycols and of polyalkylene glycols comprising C$_1$ to C$_{15}$ alkyl groups, and polyurethanes comprising at least one unit chosen from polyether and polycarbonate units, said ingredients (1) and (2) being present in said hair styling product.

31. The hair styling product according to claim 30, further comprising a cosmetically acceptable medium.

32. The hair styling product according to claim 30, wherein said at least one additive (B) is chosen from non-oxyalkylenated silicones modified with at least one group chosen from: carboxylic, alkoxy, sulphonate, thiol, hydroxyl, amino, and hydroxyacylamino groups.

33. The hair styling product according to claim 30, wherein said at least one additive (B) is chosen from unmodified non-oxyalkylenated silicones.

34. The hair styling product according to claim 33, wherein said unmodified non-oxyalkylenated silicones are chosen from polydjalkylsiloxane, polyarylsiloxane, and polyalkyl-arylsiloxane.

35. The hair styling product according to claim 30, wherein said at least one additive (B) is chosen from oxyalkylenated silicones chosen from compounds of formula (I):

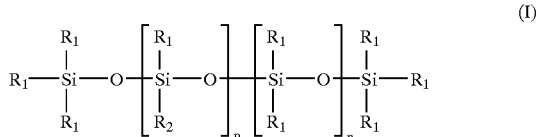

wherein:
R$_1$, which may be identical or different, is chosen from hydrogen and C$_1$–C$_{30}$ linear and branched alkyl radicals, $R_2$, which may be identical or different, is chosen from
—$(C_xH_{2x})$—$(OC_2H_4)_a$—$(OC_3H_6)_b$—$OR_3$, $R_3$, which may be identical or different, is chosen from hydrogen, linear and branched alkyl radicals containing from 1 to 12 carbon atoms, and linear and branched acyl radicals containing from 2 to 12 carbon atoms, n ranges from 0 to 1000, p ranges from 1 to 8, a ranges from 0 to 50, b ranges from 0 to 50, a+b is greater than or equal to 1, x ranges from 1 to 5, and the number-average molecular weight is greater than or equal to 15,000.

36. The hair styling product according to claim 35, wherein the number-average molecular weight ranges from about 25,000 to about 75,000.

37. The hair styling product according to claim 30, wherein said at least one additive (B) is chosen from polyurethanes chosen from:

anionic, cationic, nonionic, and amphoteric polyurethanes.

38. The hair styling product according to claim 30, wherein said at least one additive (B) is chosen from polyurethane-polyethers.

39. The hair styling product according to claim 30, wherein said at least one additive (B) is chosen from: alkyl ethers of an alkylene glycol and of a polyalkylene glycol chosen from diethylene glycol ethyl ether, diethylene glycol methyl ether, diethylene glycol butyl ether, diethylene glycol hexyl ether, dipropylene glycol butyl ether, tripropylene glycol butyl ether, dipropylene glycol ethyl ether, tripropylene glycol methyl ether and diethylene glycol methyl ether.

40. The hair styling product according to claim 30, wherein said at least one film-forming polymer (A) is present at a concentration ranging from about 0.05% to about 20% by weight, relative to the total weight of the composition.

41. The hair styling product according to claim 30, wherein said at least one film-forming polymer (A) is present at a concentration ranging from about 0.1% to about 15% by weight, relative to the total weight of the composition.

42. The hair styling product according to claim 41, wherein said at least one film-forming polymer (A) is present at a concentration ranging from about 0.25% to about 10% by weight, relative to the total weight of the composition.

43. The hair styling product according to claim 30, wherein said at least one additive (B) is present at a concentration ranging from about 0.05% to about 20% by weight, relative to the total weight of the composition.

44. The hair styling product according to claim 43, wherein said at least one additive (B) is present at a concentration ranging from about 0.1% to about 15% by weight, relative to the total weight of the composition.

45. The hair styling product according to claim 44, wherein said at least one additive (B) is present at a concentration ranging from about 0.25% to about 10% by weight, relative to the total weight of the composition.

46. The hair styling product according to claim 30, wherein the ratio of the concentration of said at least one film-forming polymer (A) to the concentration of said at least one additive (B) ranges from about 4000:1 to about 0.002:1.

47. The hair styling product according to claim 30, further comprising at least one cosmetic additive chosen from thickeners; anionic, nonionic, cationic and amphoteric surfactants; fragrances; preserving agents; sunscreens; proteins; vitamins; provitamins; fixing and non-fixing, anionic, nonionic, cationic and amphoteric polymers other than those defined in claim 30; mineral, plant and synthetic oils; ceramides; pseudoceramides; and any other suitable additive used in cosmetic compositions.

48. A process for shaping hair, said process comprising applying, in said process for shaping hair, to said hair a cosmetic composition comprising:

(1) at least one film-forming polymer (A), wherein a film obtained by drying a mixture of said at least one film-forming polymer (A) with ethanol or water, under a humid atmosphere, has a mechanical profile defined by at least:

(i) an elongation at break ($\epsilon_r$) of greater than or equal to 160%; and (ii) a recovery at 300 seconds ($R_{300}$) of greater than or equal to 45%;

(2) at least one additive (B) chosen from: linear, non-oxyalkylenated, functionalized and unfunctionalized silicones, oxyalkylenated silicones, alkyl ethers of alkylene glycols and of polyalkylene glycols comprising $C_1$ to $C_{15}$ alkyl groups, and polyurethanes comprising at least one unit chosen from polyether and polycarbonate units.

49. A process for holding or fixing a hair style, said process comprising applying to hair a cosmetic composition comprising:

(1) at least one film-forming polymer (A), wherein a film obtained by drying a mixture of said at least one film-forming polymer (A) with ethanol or water, under a humid atmosphere, has a mechanical profile defined by at least:

(i) an elongation at break ($\epsilon_r$) of greater than or equal to 160%; and (ii) a recovery at 300 seconds ($R_{300}$) of greater than or equal to 45%; and (2) at least one additive (B) chosen from: linear, non-oxyalkylenated, functionalized and unfunctionalized silicones, oxyalkylenated silicones, alkyl ethers of alkylene glycols and of polyalkylene glycols comprising $C_1$ to $C_{15}$ alkyl groups, and polyurethanes comprising at least one unit chosen from polyether and polycarbonate units, and further comprising subsequently styling said hair.

50. A hair care product comprising a composition comprising:

(1) at least one film-forming polymer (A) in said hair care product, wherein a film obtained by drying a mixture of said at least one film-forming polymer (A) with ethanol or water, under a humid atmosphere, has a mechanical profile defined by at least:

(i) an elongation at break ($\epsilon_r$) of greater than or equal to 160%; and (ii) a recovery at 300 seconds ($R_{300}$) of greater than or equal to 45%; and (2) at least one additive (B) chosen from: linear, non-oxyalkylenated, functionalized and unfunctionalized silicones, oxyalkylenated silicones, alkyl ethers of alkylene glycols and of polyalkylene glycols comprising $C_1$ to $C_{15}$ alkyl groups, and polyurethanes comprising at least one unit chosen from polyether and polycarbonate units, said ingredients (1) and (2) being present in said hair care product.

51. A process for preparing a cosmetic composition, said process comprising combining at least one additive (B) and at least one film-forming polymer (A) in a cosmetic composition, wherein a film obtained by drying a mixture of said at least one film-forming polymer (A) with ethanol or water, under a humid or dry atmosphere, has a mechanical profile defined by at least:
- (i) an elongation at break ($\epsilon_r$) of greater than or equal to 160%; and
- (ii) a recovery at 300 seconds ($R_{300}$) of greater than or equal to 45%, and wherein said at least one additive (B) is chosen from oxyalkylenated silicones chosen from compounds of formula (I):

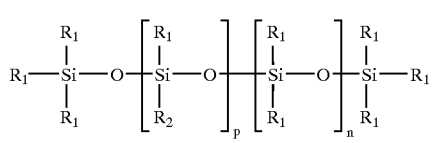

wherein:
- $R_1$, which may be identical or different, is chosen from hydrogen and $C_1$–$C_{30}$ linear and branched alkyl radicals,
- $R_2$, which may be identical or different, is chosen from —$(C_xH_{2x})$—$(OC_2H_4)_a$—$(OC_3H_6)_b$—$OR_3$,
- $R_3$, which may be identical or different, is chosen from hydrogen, linear and branched alkyl radicals containing from 1 to 12 carbon atoms, and linear and branched acyl radicals containing from 2 to 12 carbon atoms,
- n ranges from 0 to 1000,
- ranges from 1 to 8,
- a ranges from 0 to 50,
- b ranges from 0 to 50,
- a+b is greater than or equal to 1,
- x ranges from 1 to 5, and
- the number-average molecular weight is greater than or equal to 15,000.

52. A pump-dispenser bottle containing a cosmetic composition comprising:
- (1) at least one film-forming polymer (A), wherein a film obtained by drying a mixture of said at least one film-forming polymer (A) with ethanol or water, under a humid atmosphere, has a mechanical profile defined by at least:
  - (i) an elongation at break ($\epsilon_r$) of greater than or equal to 160%; and
  - (ii) a recovery at 300 seconds ($R_{300}$) of greater than or equal to 45%; and
- (2) at least one additive (B) is chosen from: linear, non-oxyalkylenated, functionalized and unfunctionalized silicones, oxyalkylenated silicones, alkyl ethers of alkylene glycols and of polyalkylene glycols comprising $C_1$ to $C_{15}$ alkyl groups, and polyurethanes comprising at least one unit chosen from polyether and polycarbonate units, said ingredients (1) and (2) being present in said pump dispenser bottle.

53. A process for obtaining a film, obtained by drying a mixture of at least one film-forming polymer (A) with ethanol or water, under a humid atmosphere, wherein said film has a mechanical profile defined by at least one of:
- (i) an elongation at break ($\epsilon_r$) of greater than or equal to 160%; and
- (ii) a recovery at 300 seconds ($R_{300}$) of greater than or equal to 45%; comprising combining said at least one film-forming polymer (A) with at least one additive (B) chosen from: oxyalkylenated silicones chosen from compounds of formula (I):

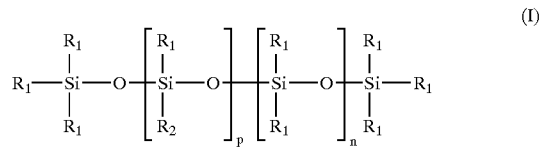

wherein:
- $R_1$, which may be identical or different, is chosen from hydrogen and $C_1$–$C_{30}$ linear and branched alkyl radicals,
- $R_2$, which may be identical or different, is chosen from —$(C_xH_{2x})$—$(OC_2H_4)_a$—$(OC_3H_6)_b$—$OR_3$,
- $R_3$, which may be identical or different, is chosen from hydrogen, linear and branched alkyl radicals containing from 1 to 12 carbon atoms, and linear and branched acyl radicals containing from 2 to 12 carbon atoms,
- n ranges from 0 to 1000,
- p ranges from 1 to 8,
- a ranges from 0 to 50,
- b ranges from 0 to 50,
- a+b is greater than or equal to 1,
- x ranges from 1 to 5, and
- the number-average molecular weight is greater than or equal to 15,000.

* * * * *

UNITED STATES PATENT AND TRADEMARK OFFICE
CERTIFICATE OF CORRECTION

PATENT NO. : 6,749,837 B1
DATED : June 15, 2004
INVENTOR(S) : Henri Samain et al.

It is certified that error appears in the above-identified patent and that said Letters Patent is hereby corrected as shown below:

Title page,
Item [57], ABSTRACT,
Line 7, "condition." should read -- conditions. --.

Column 8,
Line 51, "aldyl" should read -- alkyl --.
Lines 51-52, "polyuethanes" should read -- polyurethanes --.

Column 9,
Line 50, "0.05 to" should read -- 0.05% to --.

Column 10,
Line 50, "polydjalkylsiloxane," should read -- polydialkylsiloxane, --.

Column 12,
Line 19, after "to 45%;" insert -- and --.

Column 13,
Line 33, "ranges from 1 to 8," should read -- p ranges from 1 to 8, --.

Signed and Sealed this

Fourteenth Day of September, 2004

JON W. DUDAS
*Director of the United States Patent and Trademark Office*